(12) United States Patent
Arbiser et al.

(10) Patent No.: US 9,592,226 B2
(45) Date of Patent: Mar. 14, 2017

(54) SOLENOPSIN AND DERIVATIVES, THERAPEUTIC COMPOSITIONS; AND METHODS RELATED THERETO

(71) Applicants: EMORY UNIVERSITY, Atlanta, GA (US); MERCER UNIVERSITY, Atlanta, GA (US); UNION UNIVERSITY, Jackson, TN (US)

(72) Inventors: Jack L. Arbiser, Atlanta, GA (US); J. Philip Bowen, Atlanta, GA (US); E. Blake Watkins, Jackson, TN (US)

(73) Assignees: Emory University, Atlanta, GA (US); Mercer University, Atlanta, GA (US); Union University, Jackson, TN (US)

( * ) Notice: Subject to any disclaimer, the term of this patent is extended or adjusted under 35 U.S.C. 154(b) by 0 days.

(21) Appl. No.: 14/794,094

(22) Filed: Jul. 8, 2015

(65) Prior Publication Data

US 2015/0306082 A1    Oct. 29, 2015

Related U.S. Application Data

(63) Continuation of application No. 14/271,682, filed on May 7, 2014, now abandoned.

(60) Provisional application No. 61/820,201, filed on May 7, 2013.

(51) Int. Cl.
| | |
|---|---|
| *A61K 31/445* | (2006.01) |
| *C07D 211/10* | (2006.01) |
| *A61K 45/06* | (2006.01) |
| *C07D 211/40* | (2006.01) |
| *C07D 211/22* | (2006.01) |

(52) U.S. Cl.
CPC ............ *A61K 31/445* (2013.01); *A61K 45/06* (2013.01); *C07D 211/10* (2013.01); *C07D 211/22* (2013.01); *C07D 211/40* (2013.01)

(58) Field of Classification Search
USPC ........................................................ 514/317
See application file for complete search history.

(56) References Cited

U.S. PATENT DOCUMENTS

| | | | |
|---|---|---|---|
| 6,369,078 B1 | 4/2002 | Bowen | |
| 6,780,876 B2 * | 8/2004 | Froelich | A01N 43/40 424/405 |
| 7,799,782 B2 * | 9/2010 | Munson | C07D 231/56 514/234.5 |
| 8,168,657 B2 | 5/2012 | Bowen | |
| 2005/0038071 A1 * | 2/2005 | Bowen | A61K 31/451 514/317 |

FOREIGN PATENT DOCUMENTS

WO          03061598          7/2003

OTHER PUBLICATIONS

Blum et al. CAS:118:207238, 1993.*
Abe et al. CAS: 101: 230315, 1984.
Arbiser et al. "Solenopsin, the alkaloidal component of the fire ant (*Solenopsis invicta*), is a naturally occurring inhibitor of phosphatidylinositol-3-kinase signaling and angiogenesis" Blood, 2007, 109(2): 560-565.
Blum et al. "A new dialkylpiperidine in the venom of the fire ant *Solenopsis invicta*, Journal of Natural Toxins" 1992; 1(2): 57-63 [Abstract].
Chen et al. "Reduction of Venom Alkaloids in Solenopsis richteri Solenopsis invicta Hybrid: An Attempt to Identify New Alkaloidal Components" J. Agric. Food Chem., 2010, 58: 11534-11542.
Chen et al. "Similarity in Venom Alkaloid Chemistry of Alate Queens of Imported Fire Ants: Implication for Hybridization between Solenopsis richteri and S. invicta in the Southern United States" Chemistry & Biodiversity, 2012; 9: 702.
Eliyahu et al. "Venom alkaloid and cuticular hydrocarbon profiles are associated with social organization, queen fertility status, and queen genotype in the fire ant *Solenopsis invicta*" J Chem Ecol., 2011; 37(11): 1242-1254.
Gao et al. "PI3K/Akt signaling requires spatial compartmentalization in plasma membrane microdomains" PNAS, 2011; 108: 14509-14514.
Karlsson et al. "Novel Synthesis and Activity of Solenopsin A and Analogs, Topical Inhibitors of Phosphoinositol-3 Kinase/Akt with Ceramide-like Properties" International Investigative Dermatology Conference, 2013.
Karlsson et al. "Solenopsin A and analogs exhibit ceramide-like biological activity" Vascular Cell, 2015; 7: 5.
Park et al. "Solenopsin A, a venom alkaloid from the fire ant *Solenopsis invicta*, inhibits quorum-sensing signaling in Pseudomonas aeruginosa" Journal of Infectious Diseases, 2008; 198(8): 1198-1201.
Yi et al. "Fire Ant Venom Alkaloid, Isosolenopsin A, a Potent and Selective Inhibitor of Neuronal Nitric Oxide Synthase" International Journal of Toxicology, 2003; 22: 81-86.

* cited by examiner

*Primary Examiner* — Rei-Tsang Shiao
(74) *Attorney, Agent, or Firm* — Emory Patent Group

(57) ABSTRACT

This disclosure relates to solenopsin derivatives, pharmaceutical compositions, and therapeutic uses related thereto. In certain embodiments, the disclosure relates to compounds of the following formula:

Formula I

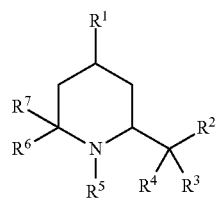

or salts, esters or prodrugs thereof as described herein.

9 Claims, 5 Drawing Sheets

SOLENOPSIN AND DERIVATIVES, THERAPEUTIC COMPOSITIONS; AND METHODS RELATED THERETO

CROSS-REFERENCE TO RELATED APPLICATIONS

This application is a Continuation of U.S. patent application Ser. No. 14/271,682 filed May 7, 2014, which claims the benefit of priority to U.S. Provisional Application No. 61/820,201 filed May 7, 2013, which applications are hereby incorporated by reference in their entireties.

ACKNOWLEDGEMENTS

This invention was made with government support under Grant No. AR047901 awarded by the National Institutes of Health. The Government has certain rights in the invention.

BACKGROUND

The racemic (+/−)-cis- and trans-isomers of 2-methyl-6-nundecylpiperidine are known as isosolenopsin A and solenopsin A, respectively. Arbiser et al. report solenopsin is an inhibitor of phosphatidylinositol-3-kinase signaling and angiogenesis. See Blood (2007) 109, 560-565.

The serine/threonine kinase c-Akt-1, or protein kinase Bα (PKB), is the cellular homolog of a transforming oncogene initially isolated from a lymphoma. Akt is a downstream target of phosphatidylinositol-3-kinase (PI3K), a family of at least 4 different enzymes, with the prototypical PI3K heterodimer consisting of a p85 (regulatory) and a p110 (catalytic) subunit. The PI3K/Akt pathway is involved in the regulation of diverse cellular functions including proliferation, cytoskeletal organization, survival, and malignant transformation. Upon binding of PI3K products to its pleckstrin homology domain, Akt is translocated to the plasma membrane where it is activated by upstream phosphorylated kinases, including PI3K-dependent kinases 1 and 2 (PDK1 and PDK2) and mammalian target of rapamycin complex 2 (mTORC2). The PI3K/Akt pathway is stimulated by numerous receptor tyrosine kinases and oncogenes, including receptors for insulin-like growth factor 1 (IGF-1), platelet-derived growth factor (PDGF), vascular endothelial growth factor (VEGF), ras, Her2/neu, and polyoma middle T oncogenes. Because Akt plays a central role in regulating apoptosis, angiogenesis, and metabolism of cells, Akt is an attractive pharmacologic target for the treatment of cancer and inflammation. Thus, there is a need to identify compound that target the PI3K/Akt pathway.

Yi et al. report that fire ant venom alkaloid, isosolenopsin A, is a potent and selective inhibitor of neuronal nitric oxide synthase. Int J Toxicol, 2003, 22(2):81-6. Chen et al., report the reduction of venom alkaloids. J Agric Food Chem, 2010, 58(22):11534-42. See also Chen et al., Chem Biodivers, 2012, 9(4):702-13.

References cited herein are not an admission of prior art.

SUMMARY

This disclosure relates to solenopsin derivatives and therapeutic uses related thereto. In certain embodiments, the disclosure contemplates topical administration. In certain embodiments, the disclosure contemplates treatment of actinic keratosis, psoriasis, squamous cell carcinoma and basal cell carcinoma. In certain embodiments, the disclosure relates to compounds of the following formula:

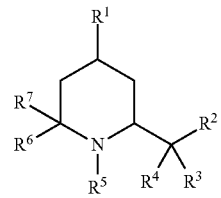

Formula I or salts, esters, or prodrugs thereof wherein:

$R^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different $R^{10}$;

$R^2$ is a long chain alkyl, hydrocarbon, or hydrophobic group, wherein $R^2$ is optionally substituted with one or more, the same or different $R^{10}$;

$R^3$ and $R^4$ are at each occurrence independently selected from hydrogen or hydroxy;

$R^5$, $R^6$, and $R^7$ are at each occurrence independently selected from hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$, $R^6$, and $R^7$ are optionally substituted with one or more, the same or different $R^{10}$;

$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to pharmaceutical compositions comprising a compound disclosed herein and a pharmaceutically acceptable excipient.

In certain embodiments, the disclosure relates to methods of treating or preventing a disorder or condition associated with Akt/PDK1 such as cancer or an inflammatory disorder comprising administering an effective amount of a compound disclosed herein to a subject in need thereof. In certain embodiments, the subject diagnosed with, exhibiting symptoms of, or at risk of cancer or an inflammatory disorder.

DETAILED DISCUSSION

Figure 1:
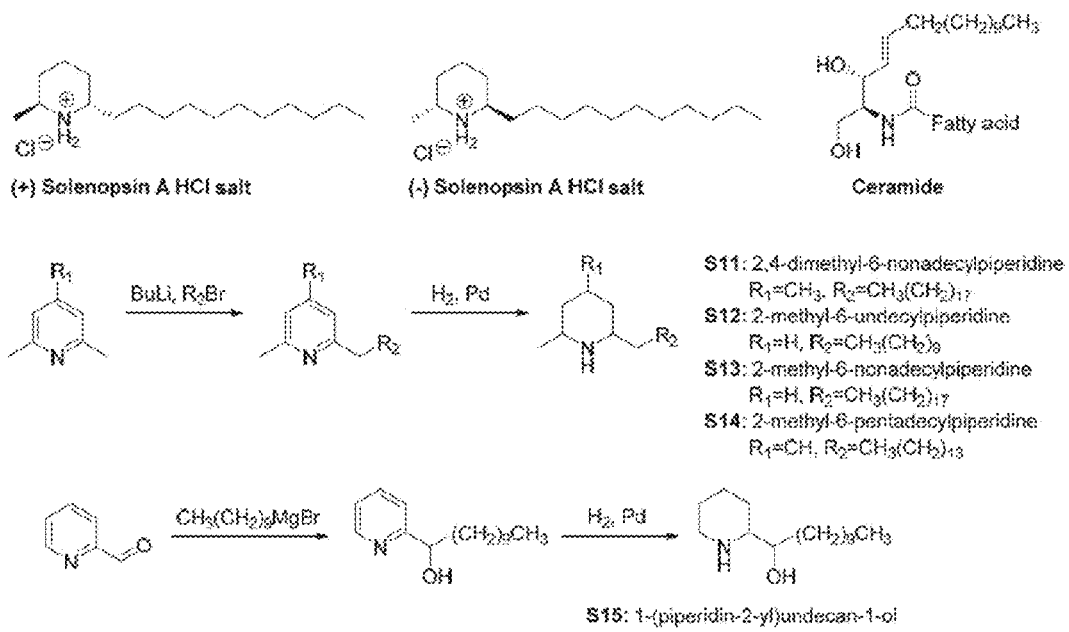
FIG. 1 illustrates synthetic procedure for preparation of compounds S11-S15. (−)-Solenopsin A is a component of the venom of the fire ant *solenopsis invicta*. (+)-Solenopsin A is the enantiomer of the naturally occurring solenopsin. The structure of solenopsin resembles the structure of ceramides, which are fatty acid amides of sphingosine that play a crucial role in homeostasis of the skin and other organs. Solenopsin analogs S11-S14 were synthesized by deprotonation of 2,6-dimethylpyridine (S12-S14) or 2,4,6-trimethylpyridine (S11) by n-butyllithium, followed by addition of alkyl bromides. Analog S15 was synthesized by treating pyridine-2-carboxaldehyde with the Grignard reagent decylmagnesium bromide. The solenopsin analogs (S11-S15) were successfully obtained after hydrogenation of the various 2-alkylpyridines.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, "alkyl" means a noncyclic straight chain or branched, unsaturated or saturated hydrocarbon such as those containing from 1 to 10 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 7 to 20 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butyryl, 2-butyryl, 1-pentynyl, 2-pentynyl, 3-methyl-1-butyryl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—$CH_3$).

"Alkanoyl" refers to an alkyl as defined above attached through a carbonyl bride (i.e., —C(=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfinyl" refers to an alkyl as defined above attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)$_2$Ra, —OS(=O)2Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, rodent, monkey or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" can be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It can also be identified by a change in relevant biomarker or gene expression profile, such as PSA for prostate cancer, HER2 for breast cancer, or others.

Solenopsin Derivatives

In certain embodiments, the disclosure relates to solenopsin derivatives that are compounds of the following formula:

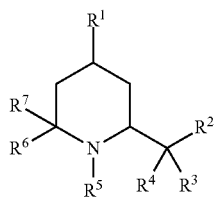

Formula I or salts, esters, or prodrugs thereof wherein:

$R^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different $R^{10}$;

$R^2$ is a long chain alkyl, hydrocarbon, or hydrophobic group, wherein $R^2$ is optionally substituted with one or more, the same or different $R^{10}$;

$R^3$ and $R^4$ are at each occurrence independently selected from hydrogen or hydroxy;

$R^5$, $R^6$, and $R^7$ are at each occurrence independently selected from hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$, $R^6$, and $R^7$ are optionally substituted with one or more, the same or different $R^{10}$;

$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^3$ or $R^4$ is hydrogen and the other is hydroxy and $R^2$ is a hydrocarbon chain comprising between 9 and 23 carbons or 10 and 23 carbons.

In certain embodiments, $R^1$ is hydrogen or alkyl.

In certain embodiments, $R^2$ is a hydrocarbon chain comprising between 9 and 23, 10 and 23 carbons, or 10 and 19 carbons.

In certain embodiments, $R^3$ or $R^4$ is hydrogen and the other is hydroxy.

In certain embodiments, $R^5$ is hydrogen.

In certain embodiments, $R^6$ and $R^7$ are at each occurrence independently selected from hydrogen or alkyl.

In certain embodiments, $R^6$ or $R^7$ are hydrogen and the other is alkyl.

In certain embodiments, $R^6$ and $R^7$ are hydrogen.

In certain embodiments, $R^6$ and $R^7$ are alkyl.

In certain embodiments, the compound is 2,4-dimethyl-6-nonadecylpiperidine;
  2-methyl-6-nonadecylpiperidine;
  2-methyl-6-pentadecylpiperidine; and
  2-decyl-6-methylpiperidine.

In certain embodiments, the compound is 1-(piperidin-2-yl)decan-1-ol and 1-(6-methylpiperidin-2-yl)decan-1-ol.

In certain embodiments, the disclosure relates to solenopsin derivatives that are compounds of the following formula:

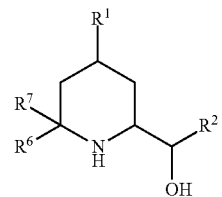

Formula IA or salts, esters, or prodrugs thereof wherein:

$R^1$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different $R^{10}$;

$R^2$ is a long chain alkyl, hydrocarbon, or hydrophobic group, wherein $R^2$ is optionally substituted with one or more, the same or different $R^{10}$;

$R^6$, and $R^7$ are at each occurrence independently selected from hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^6$, and $R^7$ are optionally substituted with one or more, the same or different $R^{10}$;

$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^3$ or $R^4$ is hydrogen and the other is hydroxy and $R^2$ is a hydrocarbon chain comprising between 9 and 23 carbons or 10 and 23 carbons.

In certain embodiments, $R^1$ is hydrogen or alkyl.

In certain embodiments, $R^2$ is a hydrocarbon chain comprising between 9 and 23 carbons.

In certain embodiments, $R^5$ is hydrogen.

In certain embodiments, $R^6$ and $R^7$ are at each occurrence independently selected from hydrogen or alkyl.

In certain embodiments, $R^6$ or $R^7$ are hydrogen and the other is alkyl.

In certain embodiments, $R^6$ and $R^7$ are hydrogen.

In certain embodiments, $R^6$ and $R^7$ are alkyl.

Uses of Solenopsin Derivatives

Solenopsin analogs can be synthesized by lithiation of the industrial dimethylpyridines, followed by alkylation of the lithiated pyridines with alkyl halides, which can be varied. Finally, the alkylated pyridine is hydrogenated to give the solenopsin analogs (FIG. 1).

The anti-proliferative potency of solenopsin A and analogs S11-S15 was assessed in three different cell lines, two human melanoma cell lines (A375 and A2058) and one murine angiosarcoma cell line (SVR). As expected, the naturally occurring (−)-solenopsin A and its enantiomer (+)-solenopsin A displayed highly anti-proliferative effect in all three cell lines (FIG. 2). Analog S12, which is a mix of the two corresponding cis-isomers of solenopsin A, was shown to have anti-proliferative properties, although not as potent as solenopsin A itself (FIG. 2). Two of the new analogs, S14 and S15, turned out to be equally as effective as solenopsin A in all three cell lines (FIG. 2).

Current topical treatments for NMSC include 5-fluorouracil and imiquimod. Imiquimod, as a toll receptor agonist, likely induces ceramide production, but does not necessarily have any effect on phosphoinositol-3 kinase/Akt activation. 5-Fluorouracil also likely induces ceramide as part of its induction of cell death, but does not directly downregulate phosphoinositol-3 kinase/Akt activation. Solenopsin and solenopsin analogs may have advantages over these current therapies by both inhibiting phosphoinositol-3 kinase/Akt activation as well as having the same downstream actions as both imiquimod and 5-fluorouracil. In addition to solenopsins anti-proliferative and anti-angiogenic effects it also inhibits quorum sensing in *Pseudomonas aeruginosa*. Given that venous ulcers in human patients are highly angiogenic, and are often colonized with *Pseudomonas*, solenopsin and solenopsin analogs may also be useful in the treatment of venous ulcers and other angiogenic disorders of the skin.

The effect of solenopsin and analogs were examined on two stereotypic sites of ceramide activity, namely at lipid rafts and mitochondria. By using a FRET-based assay we show that native (−)-solenopsin A as well as selected solenopsin analogs has ceramide-like activity at lipid rafts. Furthermore, solenopsin and solenopsin analogs cause mitophagy and superoxide generation. Solenopsin and analogs kill tumor cells regardless of PTEN status or Akt activation. Solenopsin increases Akt phosphorylation in cells with wild type p53, while it decreases Akt activation in cells with defective p53 function, thus demonstrating a context dependent effect on tumor cells. Despite elevation of Akt in solenopsin treated tumor cells with wild type p53, solenopsin killed tumor cells regardless of Akt status. Given that loss of PTEN and elevation of Akt are major mechanisms of resistance to chemotherapy, the use of solenopsin and analogs may be of great utility in killing tumor cells that exhibit these adverse prognostic markers.

Solenopsin A is a small molecular weight alkaloid that is a component of the venom of the fire ant, *Solenopsis invicta*. Studies have shown that solenopsin is an inhibitor of angiogenesis and Akt activation. See Arbiser J. L. et al., Blood (2007) 109, 560-565. FRET based reporters were used to show that solenopsin A and certain analogs disclosed herein downregulate Akt activity and PDK1 activation. Solenopsin A and analogs may have advantages over certain current therapies by both inhibiting PI3K/Akt activation as well as causing cell death through other pathways.

Solenopsin exhibited anti-angiogenic activity and downregulated phosphoinositol-3 kinase in the p53 deficient renal cell carcinoma cell line 786-O. Arbiser et al. Solenopsin, the alkaloidal component of the fire ant (*Solenopsis invicta*), is a naturally occurring inhibitor of phosphatidylinositol-3-kinase signaling and angiogenesis. Blood 109, 560-565 (2007).

In certain embodiments, this disclosure related to using compound disclosed herein for the treatment or prevention of cancer. In certain embodiments, the disclosure relates to the treatment or prevention of cancer comprising administering a compound disclosed herein to a subject in need thereof.

In certain embodiments, the disclosure relates to methods of treating or preventing actinic keratosis, psoriasis, squamous cell carcinoma or basal cell carcinoma comprising administering an effective amount of a pharmaceutical composition comprising a compound disclosed herein to a subject in need thereof.

In certain embodiments, the administration is topical to an area of skin or cancer exposed on the skin.

In certain embodiments, the subject diagnosed with, exhibiting symptoms of, or at risk of actinic keratosis, psoriasis, squamous cell carcinoma or basal cell carcinoma.

In certain embodiments, solenopsin has potential use in humans such as topical use for the treatment of angiogenic disorders of the skin, such as non-melanoma skin cancer, melanoma, and infected ulcers of chronic wounds. Chronic wounds are often highly angiogenic and colonized with *Pseudomonas aeruginosa*, and thus solenopsin might be useful in antibacterial action and modifying host inflammation.

In certain embodiments, the disclosure relates to methods of treating or preventing cancer comprising administering an effective amount of a compound disclosed herein to a subject in need thereof. In certain embodiments, the subject diagnosed with, exhibiting symptoms of, or at risk of cancer. In certain embodiments, the cancer is venous ulcers, angiogenic disorders of the skin, a hematological malignancy, a leukemia, lymphoma, acute lymphoblastic leukemia (ALL), acute myelogenous leukemia (AML), chronic lymphocytic leukemia (CLL), small lymphocytic lymphoma (SLL), chronic myelogenous leukemia, acute monocytic leukemia (AMOL), Hodgkin's lymphomas, non-Hodgkin's lymphomas, Burkitt lymphoma, B-cell lymphoma, multiple myelomacervical, ovarian cancer, colon cancer, breast cancer, gastric cancer, lung cancer, melanoma, skin cancer, ovarian cancer, pancreatic cancer, prostate cancer, head cancer, neck cancer, and renal cancer.

Solenopsin blocks quorum sensing in *Pseudomonas aeruginosa*, a common bacterium that is resistant to multiple antibiotics, and causes chronic infections, especially in the lung and skin. Park et al., Solenopsin A, a venom alkaloid from the fire ant *Solenopsis invicta*, inhibits quorum-sensing signaling in *Pseudomonas aeruginosa*. The Journal of infectious diseases 198, 1198-1201 (2008)

Quorum sensing (QS) is used by both gram-negative and gram-positive bacteria. QS is mediated by autoinducers and allows bacteria to control gene expression for a range of virulence factors, such as toxins and proteins involved in biofilm formation. Therefore, inhibiting QS signaling systems represent an attractive method for treating bacterial infections and other pathogens. See Rasmussen & Givskov, Int J Med Microbiol, 2006, 296(2-3):149-61.

In certain embodiments, this disclosure related to using compound disclosed herein for the treatment or prevention of pathogenic infections such as fungal and bacterial infections. In certain embodiments, the disclosure relates to the treatment or prevention of a fungal or bacterial infection comprising administering a compound disclosed herein to a subject in need thereof optionally in combination with another anti-fungal or anti-bacterial agent.

In certain embodiments, this disclosure related to using compound disclosed herein for the treatment or prevention of inflammatory disorders. In certain embodiments, the disclosure relates to the treatment or prevention of inflammation or an inflammatory disorder comprising administering a compound disclosed herein to a subject in need thereof. In certain embodiments, the inflammation is a result of cardiac ischemia, injury, or a pathogenic infection, e.g. viral, bacterial, fungal, or the inflammatory disorder is selected from atherosclerosis, allergies, acne vulgaris, asthma, autoimmune diseases, celiac disease, prostatitis, glomerulonephritis, hypersensitivities, inflammatory bowel disease, pelvic inflammatory disease, arthritis, rheumatoid arthritis, sarcoidosis, transplant rejection, vasculitis, or interstitial cystitis.

Yi et al. report that fire ant venom alkaloid, isosolenopsin A, is a potent and selective inhibitor of neuronal nitric oxide synthase. Int J Toxicol, 2003, 22(2):81-6. Overstimulation or overexpression of individual nitric oxide synthase isoforms plays a role in disorders including septic shock, arthritis, diabetes, ischemia-reperfusion injury, pain, and various neurodegenerative diseases. See Ji et al., J Med Chem, 2010, 53(21):7804-24, Moncada & Higgs, FASEB J, 1995, 9, 1319-1330 and Marletta et al., J. Med. Chem. 1994, 37, 1899-1907. In certain embodiments, the disclosure relates to treating or preventing septic shock, arthritis, diabetes, ischemia-reperfusion injury, pain, and neurodegenerative diseases such as Alzheimer's disease, Parkinson's disease, Huntington's disease, neuronal damage resulting from stroke, cerebral palsy, or migraine headaches comprising administering an effective amount of a compound disclosed herein to a subject in need thereof.

Combination Therapies

In certain embodiments, cancer therapeutic strategies entail pharmaceutical compositions comprising a compound disclosed herein administered in combination with a second anti-cancer agent such as gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

The cancer treatments disclosed herein can be applied as a sole therapy or can involve, conventional surgery or radiotherapy or chemotherapy. Such chemotherapy can include one or more of the following categories of antitumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family for example EGFR family tyrosine kinase inhibitors such as: N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors of phosphotidylinositol 3-kinase (PI3K) and for example inhibitors of mitogen activated protein kinase (MEK1/2) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-RAS antisense; and (viii) immunotherapy approaches, including for example ex-vivo and in-vivo approaches to increase the immunogenicity of subject tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

The combination therapy also contemplates use of the disclosed pharmaceutical compositions with radiation therapy or surgery, as an alternative, or a supplement, to a second therapeutic or chemotherapeutic agent.

A typical chronic lymphocytic leukemia (CLL) chemotherapeutic plan includes combination chemotherapy with chlorambucil or cyclophosphamide, plus a corticosteroid such as prednisone or prednisolone. The use of a corticosteroid has the additional benefit of suppressing some related autoimmune diseases, such as immunohemolytic anemia or immune-mediated thrombocytopenia. In resistant cases, single-agent treatments with nucleoside drugs such as fludarabine, pentostatin, or cladribine may be successful. Patients may consider allogeneic or autologous bone marrow transplantation. In certain embodiments, the disclosure contemplates combination treatments using compounds disclosed herein in combination with chloroambucil, cyclophosphamide, prednisone, prednisolone, fludarabine, pentostatin, and/or cladribine or combinations thereof.

Treatment of acute lymphoblastic leukemia typically includes chemotherapy to bring about bone marrow remission. Typical regiments include prednisone, vincristine, and an anthracycline drug, L-asparaginase or cyclophosphamide. Other options include tprednisone, L-asparaginase, and vincristine. Consolidation therapy or intensification therapy to eliminate any remaining leukemia may include antimetabolite drugs such as methotrexate and 6-mercaptopurine (6-MP). In certain embodiments, the disclosure contemplates combination treatments using compounds disclosed herein in combination with COP, CHOP, R—CHOP, imatinib, alemtuzumab, vincristine, L-asparaginase or cyclophosphamide, methotrexate and/or 6-mercaptopurine (6-MP). COP refers to a chemotherapy regimen used in the treatment of lymphoma of cyclophosphamide, vincristine, and prednisone or prednisolone and optionally hydroxy-daunorubicin (CHOP) and optionally rituximab (R—CHOP).

In certain embodiments, the disclosure relates to the treatment or prevention of bacterial infection comprising administering a compound disclosed herein to a subject in need thereof optionally in combination with anti-bacterial agent such as those selected from the group comprising of sulfonamides, diaminopyrimidines, quinolones, beta-lactam antibiotics, cephalosporins, tetracyclines, nitrobenzene derivatives, aminoglycosides, macrolide antibiotics, polypeptide antibiotics, nitrofuran derivatives, nitroimidazoles, nicotinin acid derivatives, polyene antibiotics, imidazole derivatives or glycopeptide, cyclic lipopeptides, glycylcyclines and oxazolidinones.

In further embodiments, these antibiotics include but are not limited to sulphadiazine, sulfones—[dapsone (DD S) and paraaminosalicyclic (PAS)], sulfanilamide, sulfamethizole, sulfamethoxazole, sulfapyridine, trimethoprim, pyrimethamine, nalidixic acids, norfloxacin, ciproflaxin, cinoxacin, enoxacin, gatifloxacin, gemifloxacin, grepafloxacin, levofloxacin, lomefloxacin, moxifloxacin, ofloxacin, pefloxacin, sparfloxacin, trovafloxacin, penicillins (amoxicillin, ampicillin, azlocillin, carbenicillin, cloxacillin, dicloxacillin, flucloxacillin, hetacillin, oxacillin, mezlocillin, penicillin G, penicillin V, piperacillin), cephalosporins (cefacetrile, cefadroxil, cefalexin, cefaloglycin, cefalonium, cefaloridin, cefalotin, cefapirin, cefatrizine, cefazaflur, cefazedone, cefazolin, cefradine, cefroxadine, ceftezole, cefaclor, cefonicid, ceforanide, cefprozil, cefuroxime, cefuzonam, cefmetazole, cefoteta, cefoxitin, cefcapene, cefdaloxime, cefdinir, cefditoren, cefetamet, cefixime, cefmenoxime, cefodizime, cefoperazone, cefotaxime, cefotiam, cefpimizole, cefpiramide, cefpodoxime, cefteram, ceftibuten, ceftiofur, ceftiolen, ceftizoxime, ceftriaxone, cefoperazone, ceftazidime, cefepime), moxolactam, carbapenems (imipenem, ertapenem, meropenem) monobactams (aztreonam) oxytetracycline, chlortetracycline, clomocycline, demeclocycline, tetracycline, doxycycline, lymecycline, meclocycline, methacycline, minocycline, rolitetracycline, chloramphenicol, amikacin, gentamicin, framycetin, kanamycin, neomicin, neomycin, netilmicin, streptomycin, tobramycin, azithromycin, clarithromycin, dirithromycin, erythromycin, roxithromycin, telithromycin, polymyxin-B, colistin, bacitracin, tyrothricin notrifurantoin, furazolidone, metronidazole, tinidazole, isoniazid, pyrazinamide, ethionamide, nystatin, amphotericin-B, hamycin, miconazole, clotrimazole, ketoconazole, fluconazole, rifampacin, lincomycin, clindamycin, spectinomycin, chloramphenicol, clindamycin, colistin, fosfomycin, loracarbef, metronidazole, nitrofurantoin and combinations thereof.

In certain embodiments, the disclosure relates to treating inflammation or an inflammatory disease or condition by administering an effective amount of a compound disclosed herein in combination with an anti-inflammatory agent such as salicylates, aspirin (acetylsalicylic acid), diflunisal, salsalate, propionic acid derivatives, ibuprofen, dexibuprofen, naproxen, fenoprofen, ketoprofen, dexketoprofen, flurbiprofen, oxaprozin, loxoprofen, acetic acid derivatives, indomethacin, tolmetin, sulindac, etodolac, ketorolac, diclofenac, nabumetone, enolic acid (oxicam) derivatives, piroxicam, meloxicam, tenoxicam, droxicam, lornoxicam, isoxicam, fenamic acid derivatives (fenamates), mefenamic acid, meclofenamic acid, flufenamic acid, tolfenamic acid, selective COX-2 inhibitors (voxibs), celecoxib, rofecoxib, valdecoxib, parecoxib, lumiracoxib, etoricoxib, firocoxib, sulphonanilides, nimesulide, licofelone, and combinations thereof.

Pharmaceutical Compositions

The compounds of the present disclosure can be administered to a subject either alone or as a part of a pharmaceutical composition.

This application claims as a novel pharmaceutical composition, all the claimed compounds combined with one or more pharmaceutical agents, as well as the combination of one or more pharmaceutical agents with any compound in the family represented by Formula I. Pharmaceutically acceptable salts, solvates and hydrates of the compounds listed are also useful in the method of the disclosure and in pharmaceutical compositions of the disclosure.

The pharmaceutical compositions of the present disclosure can be administered to subjects either orally, rectally, parenterally (intravenously, intramuscularly, or subcutaneously), intracistemally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo) and injectable organic esters such as ethyl oleate. Proper fluidity can be maintained, for example, by the use of a coating such as lecithin, by the maintenance of the required particle size in the case of dispersions and by the surfactants.

These compositions may also contain adjuvants such as preserving, emulsifying, and dispensing agents. Prevention of the action of microorganisms may be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar and as high molecular weight polyethylene glycols, and the like.

Solid dosage forms such as tablets, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be used in micro-encapsulated form, if appropriate, with one or more of the above-mentioned excipients. Controlled slow release formulations are also preferred, including osmotic pumps and layered delivery systems.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, viscoleo, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated iso-stearyl alcohols, polyoxyethylene sorbitol and sorbitan esters, microcrystalline cellulose, aluminum metahydroxide, bentonite agar-agar and tragacanth, or mixtures of these substances, and the like.

Compositions for rectal administrations are preferably suppositories which can be prepared by mixing the compounds of the present disclosure with suitable nonirritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a compound of this disclosure include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this disclosure.

Pharmaceutical compositions disclosed herein can be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure can also form internal salts, and such compounds are within the scope of the disclosure. When a compound contains a hydrogen-donating heteroatom (e.g. NH), salts are contemplated to cover isomers formed by transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases can also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein can be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Examples of structuring a compound as prodrugs can be found in the book of Testa and Caner, Hydrolysis in Drug and Prodrug Metabolism, Wiley (2006) hereby incorporated by reference. Typical prodrugs form the active metabolite by transformation of the prodrug by hydrolytic enzymes, the hydrolysis of amides, lactams, peptides, carboxylic acid esters, epoxides or the cleavage of esters of inorganic acids.

Pharmaceutical compositions typically comprise an effective amount of a compound and a suitable pharmaceutical acceptable carrier. The preparations can be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences. It is well known that ester prodrugs are readily degraded in the body to release the corresponding alcohol. See e.g., Imai, Drug Metab Pharmacokinet (2006) 21(3):173-85, entitled "Human carboxylesterase isozymes: catalytic properties and rational drug design.

Generally, for pharmaceutical use, the compounds can be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the at least one compound of the disclosure e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount," by which it is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the subject per day, more often between 0.1 and 500 mg, such as between 1 and 250 mg, for example about 5, 10, 20, 50, 100, 150, 200 or 250 mg, per kilogram body weight of the subject per day, which can be administered as a single daily dose, divided over one or more daily doses. The amount(s) to be administered, the route of administration and the further treatment regimen can be determined by the treating clinician, depending on factors such as the age, gender and general condition of the subject and the nature and severity of the disease/symptoms to be treated. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Formulations containing one or more of the compounds described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which can include plasticizers, pigments, colorants, stabilizing agents, and glidants. Delayed release, extended release, and/or pulsatile release dosage formulations can be prepared as described in standard references such as "Pharmaceutical dosage form tablets," eds. Liberman et. al. (New York, Marcel Dekker, Inc., 1989), "Remington—The science and practice of pharmacy," 20th ed., Lippincott Williams & Wilkins, Baltimore, Md., 2000, and "Pharmaceutical dosage forms and drug delivery systems," 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material can contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants can be anionic, cationic, amphoteric or nonionic surface active agents.

Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamides, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine and lauryl sulfobetaine.

If desired, the tablets, beads, granules, or particles can also contain minor amount of nontoxic auxiliary substances such as wetting or emulsifying agents, dyes, pH buffering agents, or preservatives.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS can be mixed together in any desired ratio in order to ultimately obtain a sustained-release formulation having a desirable dissolution profile. Desirable sustained-release multiparticulate systems can be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers can also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In a congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition can be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and can be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit®. (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials can also be used. Multilayer coatings using different polymers can also be applied.

The coating composition can include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates can also be used. Pigments such as titanium dioxide can also be used. Small quantities of an anti-foaming agent, such as a silicone (e.g., simethicone), can also be added to the coating composition.

Alternatively, each dosage unit in the capsule can comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that can or cannot include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles can be formulated to provide immediate release, beads and granules are generally employed to provide delayed release.

EXAMPLES

Synthesis of Solenopsin Analogs

Synthetic routes to novel solenopsin analogs were designed, using industrially available compounds. S11-S14 were synthesized by deprotonation of 2,6-dimethylpyridine (S12-S14) or 2,4,6-trimethylpyridine (S11) by n-butyllithiium, followed by addition of alkyl bromides (FIG. 1). S15 was synthesized by treating pyridine-2-carboxaldehyde with the Grignard reagent decylmagnesium bromide (FIG. 1). The solenopsin analogs (S11-S15) were successfully obtained after hydrogenation of the various 2-alkylpyridines (FIG. 1).

Investigation of the Structure-Activity Relationship

Different analogs of solenopsin were synthesized (FIG. 1) in order to explore their structure-activity relationships. The aliphatic side chains of S14 and S13 are 4 and 8 carbons longer compared to solenopsin, respectively. S11 has an 8-carbon longer side chain, as well as an extra methyl group in the 4-position of the piperidine ring. S15 has an 11-carbon side chain similar to solenopsin, but the first carbon in the side chain is hydroxylated. Also, S15 lacks the methyl group in the 2-position of the piperidine ring. All the analogs together with (−)- and (+)-solenosin A, and the isomeric mixture of the two cis-isomers of solenopsin (S12) were tested, at 10 μM, on two different human melanoma cell lines (A375 and A2058) and one murine angiosarcoma cell line (SVR) (FIG. 2). The A375 and A2058 melanoma cell lines express mutant Braf and the SVR murine angiosarcoma cell line expresses mutant Hras. One important difference between the two human melanoma cell lines is the A2058 is PTEN null, whereas A375 is not.

Figure 2A:
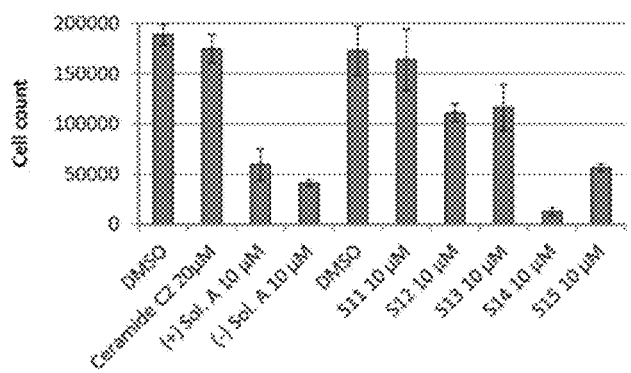
FIG. 2A shows data on anti-proliferative activity for (+)-solenopsin A ((+) Sol. A), (−)-solenopsin A ((−) Sol. A), ceramide C2, and solenopsin analogs S11-S15 in A375 cells. 50,000 cells/well were plated and treated for 24 h with each compound. The first DMSO bar in each chart serves as control for (+)-solenopsin A, (−)-solenopsin A, and ceramide C2. The second DMSO bar is the control for S11-S15. The displayed data are an average of three experiments±s.d.
Figure 2B:
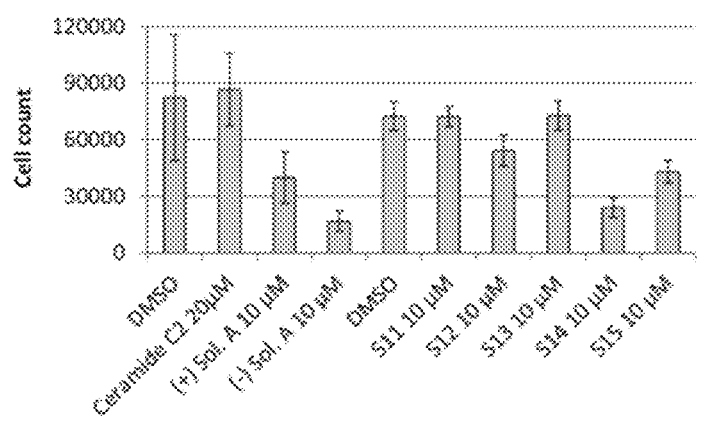
FIG. 2B shows data in SVR cells.
Figure 2C:
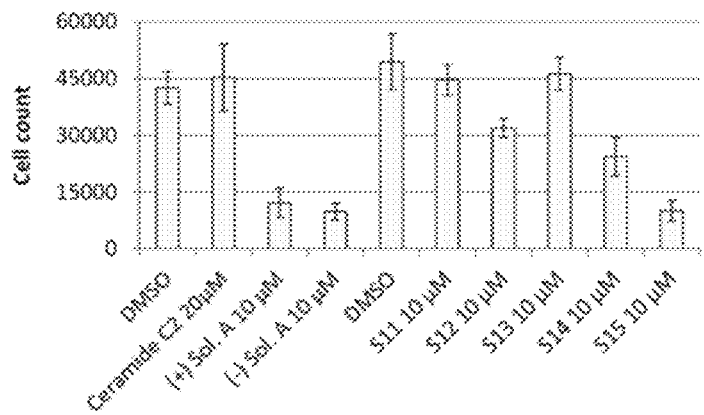
FIG. 2C shows data in A2058 cells.

No significant difference in antiproliferative potency between the naturally occurring compound, (−)-solenopsin A, and its enantiomer (+)-solenopsin A could be seen for the two human melanoma cell lines (FIGS. 2a and 2c). In the murine angiosarcoma cell line the naturally occurring (−)-solenopsin A appears to be slightly more potent than its enantiomer (+)-solenopsin A (FIG. 2b). The mixture of the two cis-isomers of solenopsin, S12, shows antiproliferative activity. However, in all three cell lines the effect is clearly weaker than for the (−)- and (+)-solenopsin A (FIG. 2), indicating that the trans-isomers have a stronger antiproliferative effect than the corresponding cis-isomers. Elongation of the aliphatic side chain with 8 carbons had a negative effect on potency, as analogs S11 and S13 displayed a lower antiproliferative effect than S12. Also, the only compound that showed no significant antiproliferative effect in any of the cell lines, compared to the control was S11, which in addition to having the longest aliphatic side chain also has an extra methyl group on the piperidine ring. Interestingly, analog S14, which has a 4 carbon longer aliphatic side chain than S12, actually turned out to be the most potent analog in A375 and SVR cells (FIGS. 2a and 2b). The most hydrophilic of the analogs, S15, did display potent antiproliferative effect in all three cell lines and in A2058 cells it was the most potent analog. In all cell lines S14 and S15 were more potent than the mixture of the cis-isomers of solenopsin A (S12) and approximately equally as potent as (−)- and (+)-solenopsin A (FIG. 2).

An optimal length of lipid side chain was noted, with a side chain optimum of 11-15 carbons, and longer side chains associated with decreased activity. Second, addition of a methyl group on the 4 position of the piperidine greatly decreased activity. Third, 2,6 disubstitution is not required, as compounds with a long side chain on the 2 position alone has activity.

Translocation of PTEN to Membrane Rafts

Phosphatase and tensin homolog (PTEN) is a natural tumor suppressor, which is commonly lost in human cancers. PTEN regulates the cell cycle by dephosphorylating PIP-3,4,5-triphosphate 3-phosphatase (PIP-3,4,5); thereby inhibiting the PI3K/Akt pathway. PTEN is preferentially localized to nonraft regions and that this is important for PI3K/Akt activity. The lipid metabolite, ceramide, is known to induce insulin resistance and although the mechanism is not clearly understood it has been shown that ceramide inhibits the PI3K/Akt pathway. It is believed that ceramide inhibits PI3K/Akt signaling by translocating PTEN from nonraft regions into lipid rafts.

Figure 3:
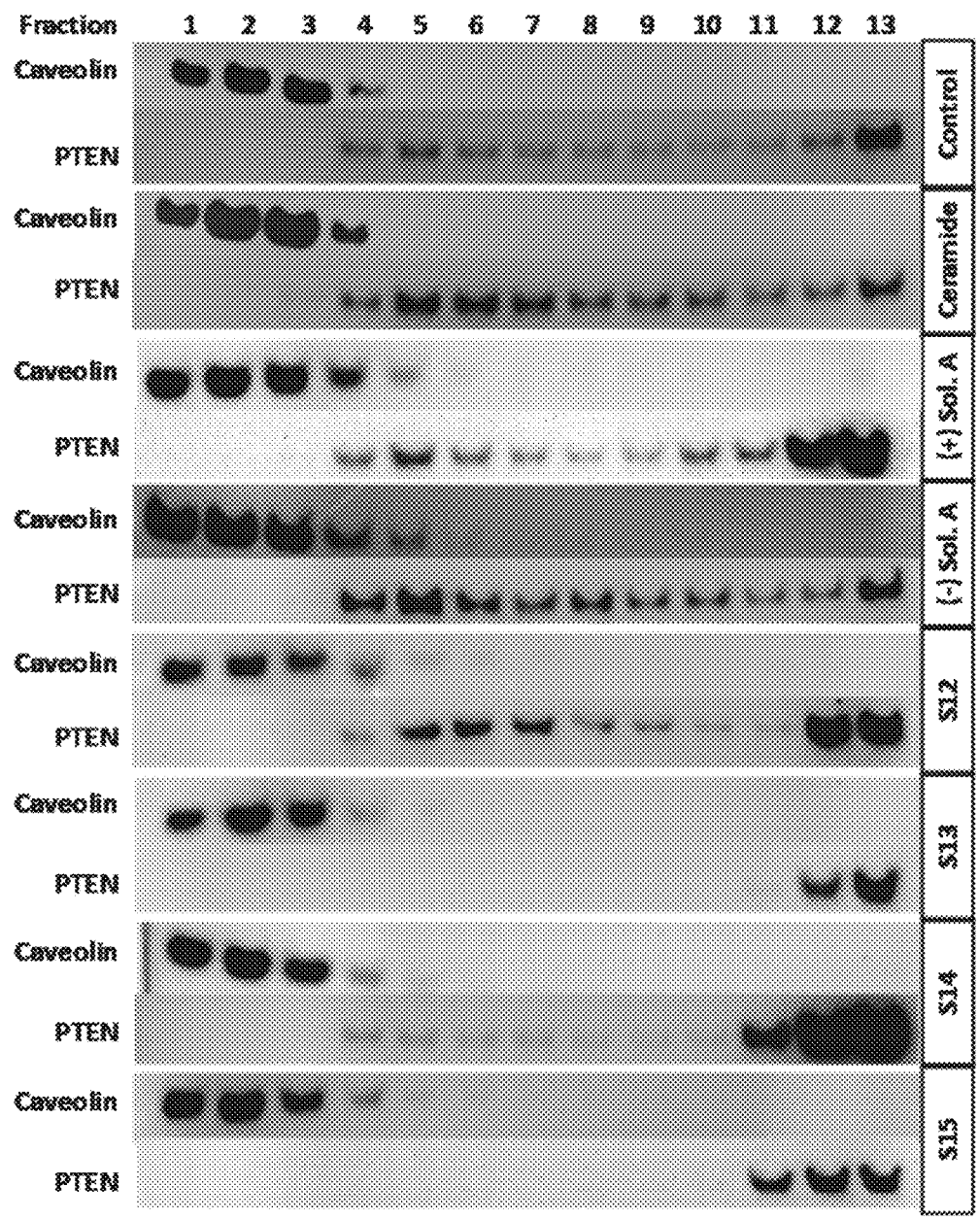
FIG. 3 shows data on lipid raft fractionation. A375 cells were treated for 1 h with: ceramide C2 (50 µM), (+)-solenopsin A ((+) Sol. A, 20 µM), (−)-solenopsin A ((−) Sol. A, 20 µM), or solenopsin analogs S11-S15 (20 µM). Cells were lysed in 0.5% Brij96 in TNEV, loaded onto the 5-40% sucrose gradient, and centrifuged at 34,000 rpm at 4° C. for 22 h. Thirteen fractions were collected, starting from the top of the tube. Equal volumes of each fraction were analyzed by Western blotting with caveolin and PTEN antibodies. Caveolin serves a positive control for which fractions that contain lipid rafts.

Caveolin was used as a positive marker to identify lipid raft fractions and an anti-PTEN antibody was used to identify PTEN-containing fractions (FIG. 3). A375 cells were treated for 1 h with 20 μM of (+)-solenopsin, (−)-solenopsin, or analogs S11-S15. Cells treated with only DMSO were used as a negative control and cells treated with 50 μM of ceramide were used as positive control. Ceramide treated cells display a higher amount of PTEN in the lipid raft fractions (fraction 1-4) (FIG. 3). The compound with the largest amount of PTEN in the raft fractions was (−)-solenopsin A (FIG. 3). (+)-Solenopsin A and analog S12 showed similar amounts of PTEN in the raft fractions as the ceramide treated group (FIG. 3). The rest of the analogs (S13-S15) appeared to have similar or even lower amounts of PTEN compared to the control group (FIG. 3).

PDK1 and Akt Activity in Membrane Rafts

Figure 4:
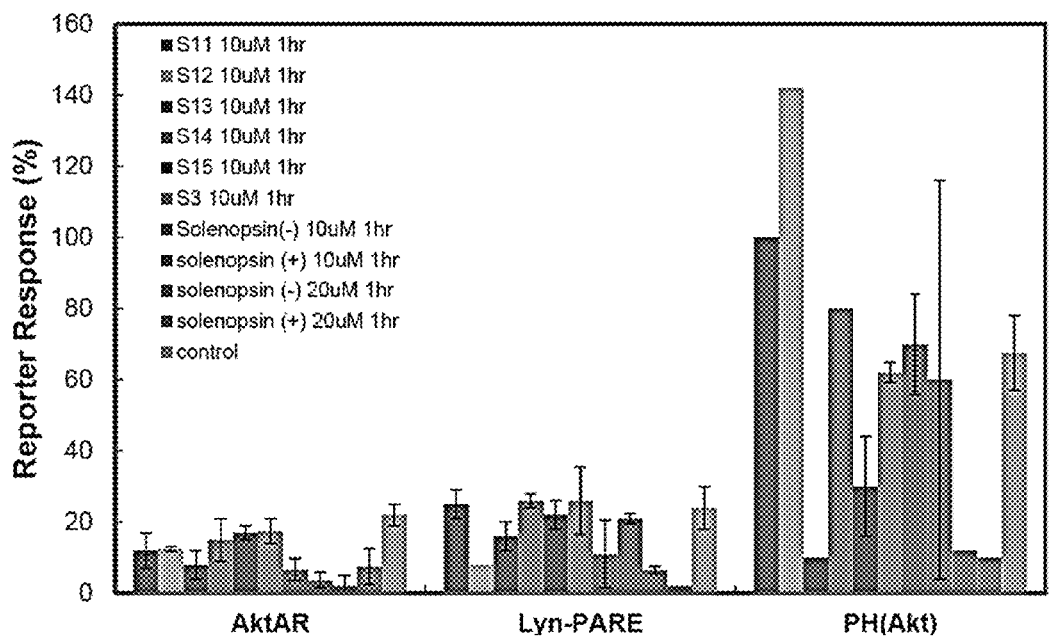
FIG. 4 shows data on inhibition of Akt activity (AktAR), PDK1 activation (Lyn-PARE), and Akt translocation (PH (Akt)-Citrine).

In order to determine whether solenopsin A and analogs have similar modes of action to ceramide, a series of fluorescent biosensors were employed for the PI3K/Akt pathway. NIH3T3 cells were treated for 1 h with (+)-solenopsin A, (−)-solenopsin A, analogs S11-S15, DMSO only (negative control), S3 (an inactive compound as negative control), or ceramide (positive control). At 20 μM concentrations both (+)- and (−)-solenopsin A inhibited Akt activity (AktAR), PDK1 activation (Lyn-PARE), and Akt translocation (PH(Akt)-citrine) to the same extent as treatment with 50 μM of ceramide (FIG. 4). At 10 μM concentrations some inhibition of Akt activity, PDK1, and Akt translocation could be seen for both (+)- and (−)-solenopsin A. At 10 μM the analog S13 also displayed some inhibition of Akt activity, PDK1 activation, as well as Akt translocation. No significant inhibition could be seen for any of the other solenopsin analogs (FIG. 4).

Figure 5:
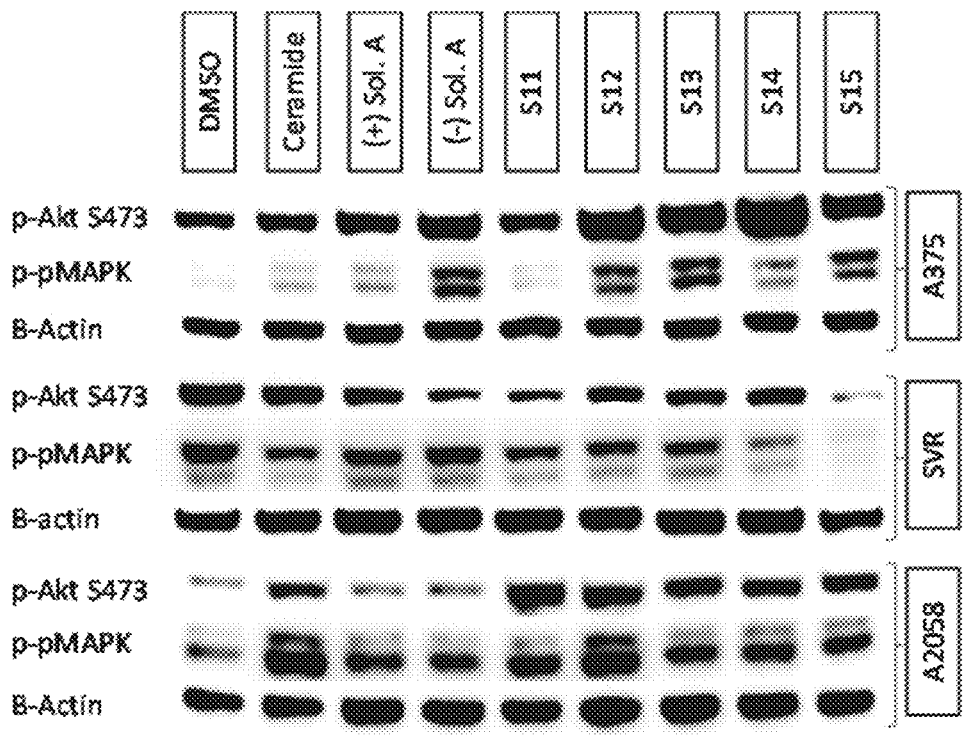
FIG. 5 shows data on the effect of solenopsin A and analogs on the expression of p-AKT and p-pMAPK 44/42. A375, SVR, and A2058 cells were treated for 24 h with ceramide C2 (20 µM), (+)-solenopsin A ((+) Sol. A, 10 µM), (−)-solenopsin A ((−) Sol. A, 10 µM), or solenopsin analogs S11-S15 (10 µM). The expression of p-AKT S473, p-pMAPK 44/42, and B-actin was determined by western blotting.

Solenopsin A and Analogs Effect on Protein Expression Varies Depending on Cell Line A375, SVR, and A2058 cells treated with solenopsin A and analogs were evaluated by Western-blotting with pAkt S473, p-pMAPK 44/42, and β-actin (FIG. 5). Although the proliferation results were more or less similar in all three cell lines, the protein expressions varied. In A375's an up-regulation of pAkt S473 and p-pMAPK 44/42 could be seen for (+)- and (−)-solenopsin A, as well as for analogs S12-S15 (FIG. 5). In SVR's on the other hand, p-Akt S473 and p-pMAPK 44/42 are down-regulated in all treatment groups, and especially in cells treated with analog S14 and S15 (FIG. 5). The results for cell line A2058 is similar to A375, i.e. there is an up-regulation of p-Akt S473 and p-pMAPK 44/42 in the treatment groups compared to the control. Phosphorylated-Akt S473 is up-regulated in all treatment groups except, (+)- and (−)-solenopsin A and p-pMAPK 44/42 is up-regulated in all treatment groups (FIG. 5). Both human melanoma cell lines (A375 and A2058) are reactive oxygen driven tumors, whereas the murine angiosarcoma cell line (SVR) is not. This may be the rationale behind the observed difference in cell signaling between these cell lines.

Solenopsin A and Analogs Affect Mitochondrial Function.

Figure 6:
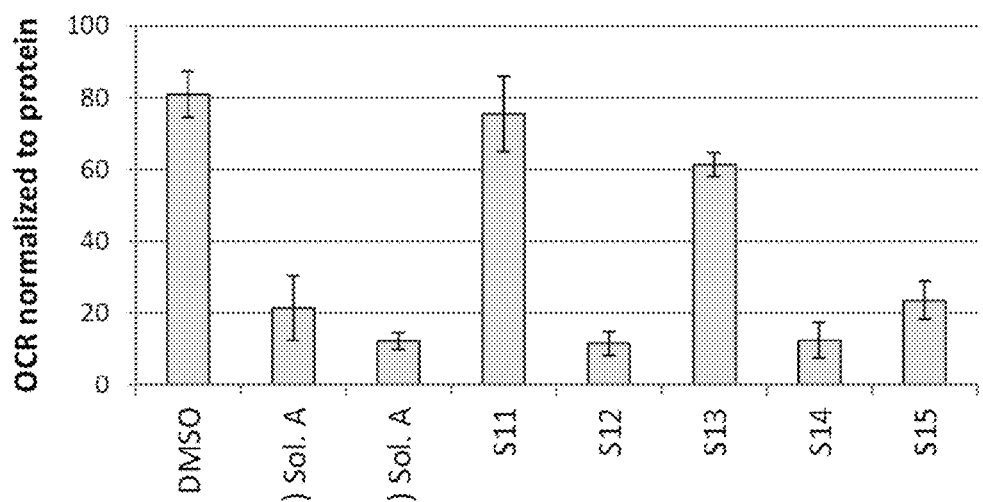
FIG. 6 shows data indicating Solenopsin A and analogs reduce oxygen consumption rate. UM-SCC1A cells were plated 15,000/well and treated for 24 h with 10 µM of (+)-solenopsin A ((+) Sol. A), (−)-solenopsin A ((−) Sol. A), and solenopsin analogs S11-S15. Oxygen consumption rate (OCR) was measured as pmoles $O_2$/minute using a Seahorse Biosciences instrument. Data shown are an average of three experiments±s.d.

Although solenopsin A recruits PTEN to lipid rafts (FIG. 4) it does not appear to be enough to dephosphorylate Akt (FIG. 5). At least not in Braf mutated cell lines, such as A375 and A2058. One possibility is that solenopsin, like ceramide, may also localize to mitochondria, and cause mitochondrial induced cell death. Cellular oxygen consumption rate can be indicative of mitochondrial function. Therefore, to investigate if solenopsin A and analogs do alter mitochondrial function, UM-SCC1A (human head and neck SCC) cells were then treated with 10 μM compound or the equivalent amount of DMSO and incubated for 24 hours. A SeaHorse Bioscience instrument was used to measure the oxygen consumption rate (OCR). This experiment show that (+)- and (−)-solenopsin A, S12, S14, and S15 have drastically reduced OCR compared to DMSO control, while S13 has a slightly reduced OCR and S11 shows little change compared to the control (FIG. 6). Mitophagy can be one reason for decreased OCR, but further assays are needed to confirm the cause for the observed differences.

Solenopsin A and Analogs Elevate ROS Levels.

Figure 7A:
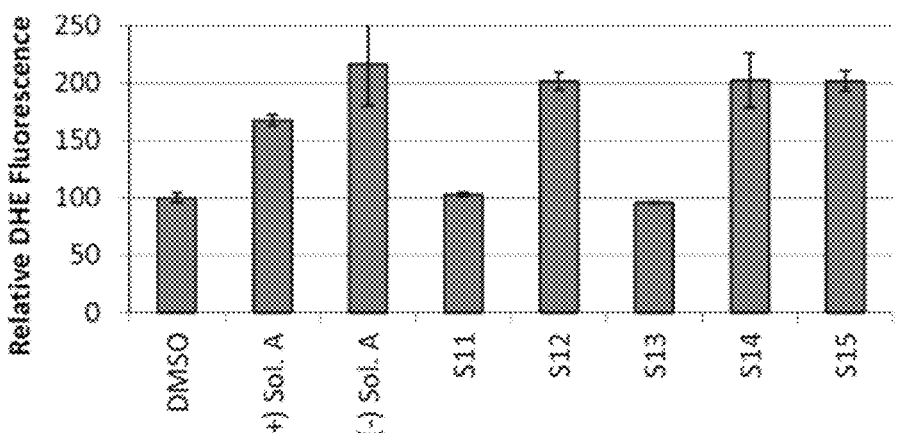
FIG. 7A shows data indicating Solenopsin A and analogs increase superoxide levels in A375 cells. Cells were treated for 24 h with 10 µM of (+)-solenopsin A ((+) Sol. A), (−)-solenopsin A ((−) Sol. A), and solenopsin analogs S11-S15. Cells were trypsined and incubated for 10 min in 10 µM dihydroethedium (DHE), followed by analysis with a FAC-Scan flow cytometer. Data shown are an average of three experiments±s.d.
Figure 7B:
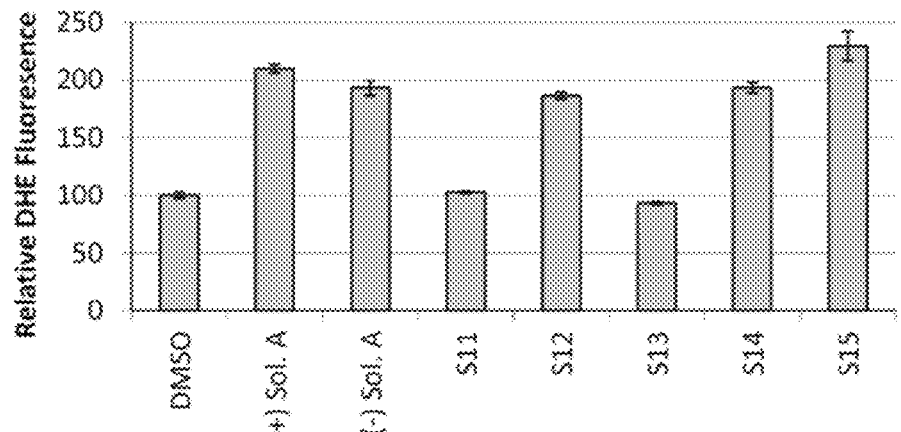
FIG. 7B shows data in SVR cells.

There was a marked increase in superoxide levels, as measured by DHE fluorescence, in A375 cells treated with the compounds (+)- and (−)-solenopsin A, S12, S14, and S15 ranging from 1.7-2.2 fold compared to vehicle treated cells (FIG. 7a). Compounds S11, and S13 had no effect on superoxide levels (FIG. 7a). Similar results were observed when compounds were tested on SVR cells (FIG. 7b).

General Procedure for Preparation of Solenopsin Analogs.

2,6-Dimethyl pyridine or 2,4,6-trimethyl pyridine (1.35 equiv.) was added dropwise to a stirred solution of n-BuLi (2M, 1.5 equiv.) in cyclohexane at 0° C. After 30 min of stirring at 0° C., the alkylbromide (1.0 equiv) was added dropwise and the reaction mixture was allowed to reach room temperature. The slurry was stirred at room temperature for another 4 h, followed by addition of ice water. The obtained water-mixture was extracted three times with ethyl acetate. The organic layers were combined and washed with brine, dried over MgSO4, filtered, and concentrated under reduced pressure. The crude compounds were purified by flash chromatography on silica gel. The resulting substituted pyridines (1.0 g) were reduced to the corresponding piperidines through catalytic hydrogenation at 50 psi for 12 hours in the presence of palladium (10 mol %) and rhodium on carbon (10 mol %) in absolute ethanol (80 mL). The mixture was filtered through Celite and concentrated under vacuum. The residue was passed through a short pad of silica, eluting with 20% (10% NH4OH:MeOH) in ethyl acetate, to give the products after concentration. 1H NMR of compounds S11-S14 showed the presence of a single diastereomer.

S11 (2,4-Dimethyl-6-nonadecylpiperidine). Compound S11 was prepared from 2.5 mL of 2,4,6-trimethyl pyridine (19 mmol) and 4.8 mL of 1-bromooctadecane (14 mmol) according to the general procedure. The crude 2,4-dimethyl-6-nonadecylpyridine was purified by flash chromatography (silica: ethyl acetate/hexanes 1:19), which afforded 2,4-dimethyl-6-nonadecylpyridine, the S11 precursor, as an off-white solid (3.71 g, 71% yield). $^1$H NMR (CDCl$_3$) δ: 6.76 (d, 2H, J=6.4), 2.67 (t, 2H, J=8.0), 2.46 (s, 3H), 2.25 (s, 3H), 1.70-1.57 (m, 2H), 1.37-1.15 (m, 32H), 0.86 (t, 3H, J=7.0). UPLC-MS (ESI): 374.4 (M+H$^+$).

Hydrogenation according to the general procedure gave the product (S11) as a white solid (893 mg, 88%). mp 56.3-57.2° C. $^1$H NMR (CDCl$_3$, 400 MHz) δ: 2.69-2.64 (m, 1H), 2.54-2.48 (m, 1H), 1.66-1.58 (m, 2H), 1.52-1.42 (m, 1H), 1.40-1.25 (m, 36), 1.09 (d, 3H, J=6.0), 0.89 (m, 6H), 0.75-0.64 (m, 2H). UPLC-MS (ESI): 380.4 (M+H$^+$).

S12 (2-Methyl-6-undecylpiperidine)

Compound S12 was prepared from 3.0 mL of 2,6-dimethyl pyridine (26 mmol) and 4.0 mL of 1-bromodecane (19 mmol) according to the general procedure. The crude 2-methyl-6-undecylpyridine was purified by flash chromatography (silica: ethyl acetate/hexanes 1:9), which afforded 2-methyl-6-undecylpyridine, the S12 precursor, as a yellow oil (2.63 g, 60% yield). $^1$H NMR (CDCl$_3$) δ: 7.47 (t, 1H, J=7.6), 6.96-6.93 (m, 2H), 2.74 (t, 2H, J=8.0), 2.52 (s, 3H), 1.73-1.67 (m, 2H), 1.37-1.25 (m, 18H), 0.88 (t, 3H, J=7.0). UPLC-MS (ESI): 248.2 (M+H$^+$). Hydrogenation according to the general procedure gave the product (S12) as a clear oil which solidified upon cooling (832 mg, 81%). $^1$H NMR (CDCl$_3$, 400 MHz) δ: 2.66-2.61 (m, 1H), 2.51-2.45 (m, 1H), 1.79-1.74 (m, 1H), 1.66-1.57 (m, 2H), 1.35-1.25 (m, 21H), 1.09-1.08 (d, 3H, J=4.4), 1.06-0.98 (m, 2H), 0.88 (t, 3H, J=7.2). UPLC-MS (ESI): 254.1 (M+H$^+$). $^1$H NMR and $^{13}$C NMR were according to the literature.

S13 (2-Methyl-6-nonadecylpiperidine). Compound S13 was prepared from 2.2 mL of 2,6-dimethyl pyridine (19 mmol) and 4.8 mL of 1-bromooctadecane (14 mmol) according to the general procedure. The crude 2-methyl-6-nonadecylpyridine was purified by flash chromatography (silica: ethyl acetate/hexanes 1:9), which afforded 2-methyl-6-nonadecylpyridine, the S13 precursor, as an off-white solid (4.57 g, 91% yield). $^1$H NMR (CDCl$_3$) δ: 7.45 (t, 1H, J=7.6), 6.94-6.91 (m, 2H), 2.72 (t, 2H, J=8.0), 2.51 (s, 3H), 1.70-1.64 (m, 2H), 1.37-1.15 (m, 32H), 0.88 (t, 3H, J=6.8). UPLC-MS (ESI): 360.4 (M+H$^+$). Hydrogenation according to the general procedure gave the product (S13) as a white solid (859 mg, 84%). mp 46.5-47.3° C. $^1$H NMR (CDCl$_3$, 400 MHz) δ: 2.65-2.62 (m, 1H), 2.50-2.48 (m, 1H), 1.78-1.74 (m, 1H), 1.66-1.58 (m, 2H), 1.37-1.25 (m, 37H), 1.08-1.07 (d, 3H, J=4.4), 1.05-0.95 (m, 2H), 0.88 (t, 3H, J=6.4). UPLC-MS (ESI): 366.3 (M+H$^+$).

S14 (2-Methyl-6-pentadecylpiperidine). Compound S14 was prepared from 2.2 mL of 2,6-dimethyl pyridine (19 mmol) and 4.1 mL of 1-bromotetradecane (14 mmol) according to the general procedure. The crude 2-methyl-6-pentadecylpyridine was purified by flash chromatography (silica: ethyl acetate/hexanes 1:20), which afforded 2-methyl-6-pentadecylpyridine, the S14 precursor, as a clear oil (4.2 g, 99%). $^1$H NMR (CDCl$_3$) δ: 7.45 (t, 1H, J 7.6), 6.94-6.91 (m, 2H), 2.72 (t, 2H, J=8.0), 2.51 (s, 3H), 1.70-1.62 (m, 2H), 1.35-1.19 (m, 24H), 0.88 (t, 3H, J=6.8). UPLC-MS (ESI): 304.2 (M+H$^+$). Hydrogenation according to the general procedure gave the product (S14) as a clear oil (839 mg, 82%). $^1$H NMR (CDCl$_3$, 400 MHz) δ: 2.62-2.61 (m, 1H), 2.48-2.46 (m, 1H), 1.77-1.74 (m, 1H), 1.64-1.57 (m, 2H), 1.35-1.25 (m, 29H), 1.06-1.05 (d, 3H, J=6.0), 1.04-0.95 (m, 2H), 0.88 (t, 3H, J=6.8). UPLC-MS (ESI): 310.3 (M+H+).

S15 (1-(Piperidin-2-yl)undecan-1-ol). Pyridine-2-carboxaldehyde (5.0 mL, 52 mmol) was added dropwise to a stirred solution of decylmagnesium bromide (52 mmol) in diethyl ether (52 mL) at 0° C. The reaction mixture was allowed to reach room and after stirring at room temperature for an additional 4 h the reaction was quenched by addition of ice water. The mixture was extracted with diethyl ether, dried over MgSO$_4$, filtered, and concentrated under reduced pressure. The crude product was purified by flash chromatography on silica gel (ethyl acetate/hexanes 1:4), which afforded 1-(pyridin-2-yl)undecan-1-ol, the S15 precursor, as an off-white solid (4.5 g, 35%). $^1$H NMR (CDCl$_3$) δ: 8.52 (d, 1H, J=5.6), 7.65 (t, 1H, J=7.6), 7.23 (d, 1H, J=7.6), 7.17 (dd, 1H, J=7.6, 5.6), 4.71 (dd, 1H, J=7.6, 4.4), 4.13 (bs, 1H, —OH), 1.84-1.60 (m, 2H), 1.42-1.18 (m, 16H), 0.85 (t, 3H, J=7.0). UPLC-MS (ESI): 250.3 (M+H$^+$).

Hydrogenation according to the general procedure gave the product (S15) as a white solid (903 mg, 88%). 1H NMR showed the product to be a 7:3 mixture of diastereomers.

Cells and Culture Conditions.

In this study five different cell lines were used: human A375 melanoma cells, human A2058 melanoma cells, immortalized murine endothelial SVR cells, 22-24 murine embryonic NIH3T3 fibroblast cells, and human UM-SCC1A squamous carcinoma cells. Cell lines were grown in DMEM with 10% fetal bovine serum.

Proliferation Studies.

A375 (human melanoma), A2058 (human melanoma), or SVR (murine angiosarcoma) cells were plated at a concentration of 50,000 cells/well. The cells were treated with 10 μM of (−)-solenopsin A, (+)-solenopsin A, or analogs (S11-S15) for 24 hours, at which point cells were counted with a Coulter Counter.

Sucrose Density Gradient Fractionation.

Cells were grown in T-75 flasks until 80% confluent followed by treatment for 1 h with 20 μM DMSO solutions of (+)-solenopsin A, (−)-solenopsin A, analogs (S12-S15), or 50 μM of ceramide C2 in DMSO. Lipid raft fractionation was performed with a 5-40% sucrose discontinuous gradient. The A375 cells from each treatment group were subjected to mechanical disruption with 8 strokes of a homogenizer and lysed for 30 min on ice in 650 μL 0.5% Brij96 in TNEV buffer (10 mM Tris•HCl, pH 7.5, 150 mM NaCl, 5 mM EDTA, 2 mM Na vanadate, and protease inhibitor cocktail). The homogenates were centrifuged at 1000 rpm for 1 min at 4° C. Supernatant (500 μL) was diluted 1:1 with 80% sucrose in TNEV buffer and transferred to a centrifuge tube (13×51 mm). Next, a layer of 35% sucrose in TNEV buffer (3 mL) was carefully placed on top of the first layer, followed by a 5% sucrose layer in TNEV buffer (1 mL). The sucrose gradient tube was centrifuged at 34,000 rpm for 22 h at 4° C. in a Beckman SW 50.1 rotor. After ultracentrifugation, thirteen 385 μL fractions were collected, starting from the top of the tube. Equal volumes of each fraction were analyzed by Western blot with relevant antibodies.

FRET Constructs.

PARE was generated by sandwiching full-length PDK1 between a fluorescent protein pair (FRET pair), ECFP and citrine, and a motif generated from the Lyn-kinase gene was added to the 5'-end to target the construct to raft microdomains. AktAR was generated by a fluorescent protein pair, cerulean and cpVE172, sandwiching a forkhead-associated binding domain (FHA1) and an Akt substrate domain (FOXO). PH(Akt)-citrine was constructed by attaching the yellow fluorescent protein (citrine) to the C-terminus of PH domain of Akt1, therefore the translocation of Akt PH domain can be detected by increase of yellow fluorescence at plasma membrane.

Cell Transfection and Imaging.

NIH3T3 cells were plated and grown to 40% confluency. Cells were transfected with Lipofectamine 2000 and serum-starved for 24 hours. For imaging, cells were washed with Hank's balanced salt solution buffer once quickly, then imaged in dark at room temperature in HBSS supplemented with solenopsin derivatives at indicated concentrations. Images were acquired on a Zeiss Axiovert 200M microscope with a cooled charge-coupled device camera. The data was analyzed with Metafluor 6.2 software (Universal Imaging, Downingtown, Pa.). Cell regions were selected and fluorescence images were background-corrected by deducting the background (regions with no cells) from the emission intensities of CFP or YFP. For analysis of Akt activity (AktAR) and PDK1 activation (LynPARE), FRET ratio of regions of interest (ROI) at cell cytosol and at cell periphery representing the plasma membrane were used, respectively. For analysis of PH (Akt) domain translocation (PH(Akt)-citrine), the ratio of intensities of citrine at cell membrane and cytosol were calculated after background correction. All the ratios were normalized with the ratio before PDGF (Sigma-Aldrich) addition.

Western Blot Analysis.

Cells were grown in T-25 flasks until 80% confluent followed by treatment for 24 h with 10 μM DMSO solutions of (+)-solenopsin A, (−)-solenopsin A, or analogs (S11-S15). Sample aliquots normalized for protein quantities were size fractionated by 10% SDS-PAGE, and the proteins were transferred to a PVDF membrane. The blots were incubated in blocking solution; TBS with 5% (wt/vol) powdered nonfat milk for 1 h at room temperature, followed by incubation over night with rabbit polyclonal p-Akt S473, p-pMAPK 44/42, B-actin, caveolin-1, and PTEN.

Measurement of OCR.

UM-SCC1A cells were plated 15,000 per well in 200 μl DMEM supplemented with 10% FBS and 1% penicillin-streptomycin in each well of a 96-well Seahorse plate and incubated overnight at 37° C. with 5% CO$_2$. Cells were then treated with 10 μM compound or the equivalent amount of DMSO and incubated for 24 hours. OCR was measured as pmoles O$_2$/minute using the Seahorse Biociences instrument per manufacturer's instructions. Protein amounts in each well were then quantified using the Thermo Scientific Pierce Protein Assay, per manufacturer's instructions.

Measurement of ROS with DHE.

A375 or SVR cells were plated in 6 cm dishes. After cells had adhered to the plates, they were treated for 24 h with 10 μM DMSO solutions of (+)-solenopsin A, (−)-solenopsin A, or analogs (S11-S15) at which time the media was aspirated. Cells were washed with 2 mL PBS then treated with 0.05% trypsin/0.53 mM EDTA (Fisher) for 3 min at RT. Cells were collected and then pelleted at 600 g for 2 min. The supernatant was aspirated and the cells were suspended in 10 uM dihydroethidium (DHE) (Life Technologies) and incubated for 10 min in the dark at RT while shaking Following this incubation, cells were kept until counting on a Becton Dickinson FACScan flow cytometer. 10,000 cells were counted and analyzed by FlowJo 7.6.4. Mean values of DHE fluorescence intensity were compared.

The invention claimed is:

1. A pharmaceutical composition in a form selected from a tablet, capsule, and pill comprising 1-(piperidin-2-yl)decan-1-ol or salt thereof and a pharmaceutically acceptable excipient.

2. A method of treating leukemia comprising administering an effective amount of pharmaceutical composition comprising 1-(piperidin-2-yl)decan-1-ol or salt thereof to a subject in need thereof.

3. The method of claim 2, wherein the leukemia is selected from acute lymphoblastic leukemia (ALL), acute myelogenous leukemia (AML), chronic lymphocytic leukemia (CLL), chronic myelogenous leukemia, and acute monocytic leukemia (AMOL).

4. The method of claim 2 wherein the compound is administered in combination with a second anti-cancer agent.

5. The method of claim 4, wherein the second anti-cancer agent is gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

6. A method of treating melanoma or skin cancer comprising administering an effective amount of pharmaceutical composition comprising 1-(piperidin-2-yl)decan-1-ol of salt thereof to a subject in need thereof.

7. The method of claim 6, wherein the subject diagnosed with, exhibiting symptoms of, or at risk of actinic keratosis, psoriasis, squamous cell carcinoma or basal cell carcinoma.

8. The method of claim 6 wherein the compound is administered in combination with a second anti-cancer agent.

9. The method of claim 8, wherein the second anti-cancer agent is gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

* * * * *